United States Patent [19]
Bitensky et al.

[11] Patent Number: 6,162,396
[45] Date of Patent: Dec. 19, 2000

[54] BLOOD STORAGE DEVICE AND METHOD FOR OXYGEN REMOVAL

[75] Inventors: Mark W. Bitensky, Waban; Tatsuro Yoshida, Newton, both of Mass.

[73] Assignee: The Regents of the University of California, Los Alamos, N. Mex.

[21] Appl. No.: 08/847,859

[22] Filed: Apr. 26, 1997

[51] Int. Cl.$^7$ .................................................. A61M 1/14
[52] U.S. Cl. .................. 422/44; 435/2; 604/403; 604/408; 604/410
[58] Field of Search ................... 422/44, 48; 604/408, 604/410, 403, 4, 405, 406, 409, 416; 435/2

[56] References Cited

U.S. PATENT DOCUMENTS

| | | | |
|---|---|---|---|
| 4,670,013 | 6/1987 | Barnes et al. | 604/403 |
| 5,037,419 | 8/1991 | Valentine et al. | 604/408 |
| 5,386,014 | 1/1995 | Nho et al. | 530/385 |
| 5,529,821 | 6/1996 | Ishikawa et al. | 428/36.91 |
| 5,624,794 | 4/1997 | Bitensky et al. | 435/2 |
| 5,691,452 | 11/1997 | Gawryl et al. | 530/385 |
| 5,698,250 | 12/1997 | DelDuca et al. | 426/124 |
| 5,811,142 | 9/1998 | DelDuca et al. | 426/424 |

*Primary Examiner*—Krisanne Thornton
*Attorney, Agent, or Firm*—Samuel M. Freund

[57] ABSTRACT

The present invention relates to a storage device and method for the long-term storage of blood and, more particularly, to a blood storage device and method capable of removing oxygen from the stored blood and thereby prolonging the storage life of the deoxygenated blood.

6 Claims, 5 Drawing Sheets

BLOOD STORAGE DEVICE AND METHOD FOR OXYGEN REMOVAL

STATEMENT REGARDING FEDERAL RIGHTS

This invention was made with government support under Contract No. W-7405-ENG-36 awarded by the U.S. Department of Energy to The Regents of the University of California. The government has certain rights in the invention.

FIELD OF THE INVENTION

The present invention relates to a storage device and, method for the long-term storage of blood and more particularly, to a blood storage device and method capable of removing oxygen from the stored blood and thereby prolonging the storage life of the deoxygenated blood.

BACKGROUND OF THE INVENTION

Adequate blood supply and the storage thereof is a problem facing every major hospital and health organization around the world. Often, the amount of blood supply in storage is considerably smaller than the need therefor. This is especially true during crisis periods such as natural catastrophes, war and the like, when the blood supply is often perilously close to running out. It is at critical times such as these that the cry for more donations of fresh blood is often heard. However, unfortunately, even when there is no crisis period, the blood supply and that kept in storage must be constantly monitored and replenished, because stored blood does not maintain its viability for long.

Stored blood undergoes steady deterioration which is, in part, caused by hemoglobin oxidation and degradation and adenosine triphosphate (ATP) depletion. Oxygen causes hemoglobin carried by the red blood cells (RBCs) to convert to met-Hb, the breakdown of which produces toxic products such as hemichrome, hemin and free $Fe^{3+}$. Together with the oxygen, these products catalyze the formation of hydroxyl radicals (OH•), and both the OH• and the met-Hb breakdown products damage the red blood cell lipid membrane, the membrane skeleton, and the cell contents. As such, stored blood is considered unusable after 6 weeks, as determined by the relative inability of the red blood cells to survive in the circulation of the transfusion recipient.

Many patents have addressed different aspects of blood storage. One such patent is U.S. Pat. No. 4,837,047 to Sato et al. which relates to a container for storing blood for a long period of time to keep the quality of the blood in good condition. The patent is directed at improving the storage life of the stored blood by maintaining a partial pressure of carbon dioxide gas in the blood at a low level. Such partial pressure is apparently obtained through normalization with the outside atmosphere. The container is made of a synthetic resin film which has a high permeability to carbon dioxide gas for the purpose of making it possible for the carbon dioxide gas to easily diffuse from the blood to outside. However, the problems caused by the interaction of the oxygen and hemoglobin in the blood are not addressed.

Another patent, U.S. Pat. No. 5,529,821 to Ishikawa et al. relates to a container and a method for the storage of blood to prevent adhesion of the blood to the container. Blood is stored in containers composed of a sheet material having a plurality of layers where a first sheet which contacts the blood substantially prevents the activation and adhesion of blood platelets to the layer. Again, however, the problems caused by the interaction of the oxygen and hemoglobin in the blood are not addressed.

There is, therefore, a need to be able to store blood on a long-term basis without the stored blood undergoing the harmful effects caused by the oxygen and hemoglobin interaction. Furthermore, the blood storage devices and methods must be simple, inexpensive and capable of long-term storage of the blood supply.

SUMMARY OF THE INVENTION

Accordingly, it is an object of the present invention to provide a blood storage device and a method of using that device which is capable of removing oxygen from the stored blood.

Furthermore, it is another object of the present invention to prevent oxygen from the storage environment from reaching the stored blood.

It is yet another object to provide a blood storage device that is simple, inexpensive and suitable for long-term storage of blood.

To achieve the foregoing and other objects, and in accordance with the purposes of the present invention, as embodied and broadly described herein, the present invention is directed to a device and method for the storage of red blood cells wherein the oxygen content of red blood cells, or other red blood cell containing blood products, can be reduced substantially below, that is at least about 50% below, the oxygen content of freshly drawn venous blood. In removing oxygen from the RBC, the heme moiety of hemoglobin is substantially free of any other ligand that would release 2,3-diphosphoglycerate (2,3-DPG) from hemoglobin, that is 2,3-DPG remaining bound to hemoglobin under these circumstances so that it can cause feedback inhibition of the RBC glycolytic pathway. In a preferred embodiment, the oxygen content of the red blood cells is thereby reduced to levels below about 15% of full saturation levels, more preferably to levels no greater than about 5–10%, and even more preferably below about 1% or even less. Such reduction in the oxygen content of the red blood cells can achieve about 75% survival rate of the red blood cells at 24 hours post-transfusion when the cells have been stored for periods greater than 5 weeks. Moreover, such survival characteristics are even achievable when the cells have been stored for 10 to 15 weeks.

The blood storage device of this invention has an oxygen impermeable outer layer that is constructed of a material having a high tensile strength to resist breakage. The material can be transparent or opaque. If opaque, a small observation window made of a transparent material can optionally be provided. Further, the blood storage device has, inside the outer layer, an RBC-compatible inner layer which contacts the stored blood. This inner layer is constructed of a material that is oxygen permeable if the oxygen scrubber is placed between the outer and inner layer and can optionally contain a plasticizer. If the plasticizer is not incorporated into the material from which the inner layer is composed, then a ribbon or strip of plasticizer-containing material can be contained within the inner layer of the device, i.e., in the compartment where the blood/RBCs are contained. This ribbon or strip is likewise composed of an RBC-compatible material.

The blood storage device also contains an oxygen scrubber material which will absorb the oxygen released from the RBCs. The oxygen scrubber material can be present as a layer between the oxygen-impermeable outer layer of the device and the oxygen-permeable inner layer of the device. Alternatively, the oxygen scrubber material can be contained in the same compartment where the blood/RBCs are contained, but the material is encapsulated within an oxygen-permeable and RBC-compatible material. This latter configuration is exemplified by having a separate bag containing the oxygen scrubber material placed inside the inner layer of the blood storage device. Any other suitable configuration is contemplated by the invention so long as the oxygen released from the RBCs and any small amount of oxygen that leaks through the outer layer can be absorbed by the oxygen scrubber material and no exogenous oxygen can reach the RBCs. Hence, the oxygen scrubber can be placed between the outer and inner layer or inside of both layers in accordance with different embodiments of the invention. The oxygen scrubber is any material capable of absorbing oxygen and includes oxygen sorbents such as, but not limited to, iron powders.

The blood storage device has at least two ports, and preferably only two ports, by which blood or RBCs can be introduced into the device by using conventional sterile connections to the ports. In this embodiment, the device can contain anticoagulant solutions and any other substances used in blood collection. Alternatively, processed blood can be transferred into the blood storage device before or after oxygenation. In this regard, it is important to note that the amount of oxygen scrubber needed in the blood storage device varies as a function of the degree of oxygenation of the blood or RBCs introduced into the device.

The present invention and its features and advantages will become more apparent from the following detailed description with reference to the accompanying drawings.

DETAILED DESCRIPTION OF THE INVENTION

Figure 1:
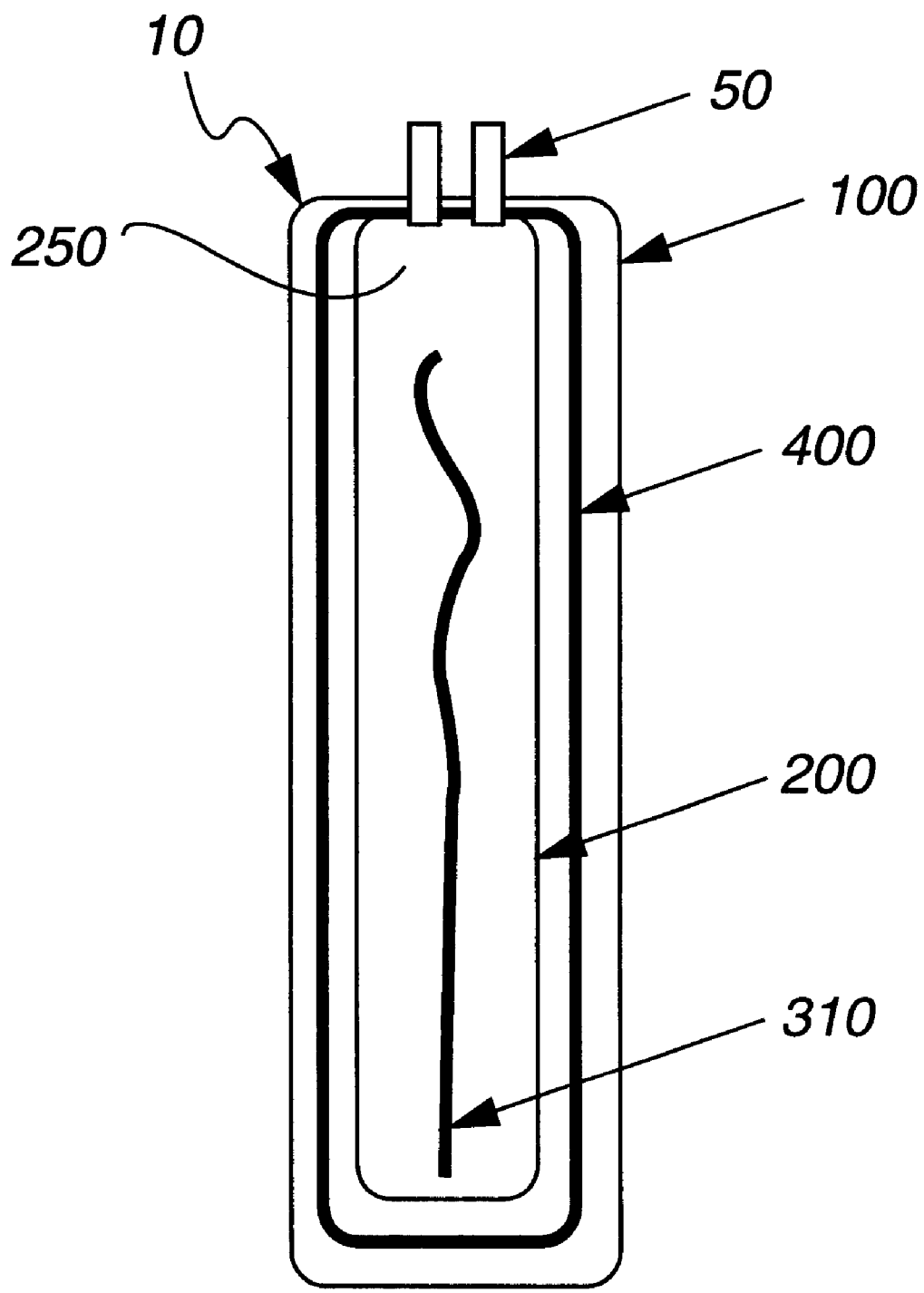
FIG. 1 illustrates a side view of a blood storage device having an oxygen scrubber material between an outer oxygen impermeable layer and a plasticizer-free, inner oxygen permeable layer with ribbon containing the plasticizer in the inner chamber of the blood storage device.

Accordingly, the present invention is directed to a blood storage device for the storage of red blood cells adapted to allow the oxygen content of RBCs to be reduced substantially below the oxygen content of freshly drawn venous blood, wherein the heme moiety of hemoglobin is substantially free of any other ligand that releases bound 2,3-DPG so that it can cause feedback inhibition of the glycolytic pathway of said cells. Moreover, by removing residual oxygen bound to hemoglobin, cellular 2,3-DPG concentration is lowered by binding to hemoglobin further relieving the feedback inhibiton caused by 2,3-DPG. The blood storage device is adapted for storage of RBCs which have already been depleted of oxygen and are to be stored under conditions which maintain or further reduce the oxygen content of the RBCs, and for storage of the so-treated RBCs under conditions which maintain or further reduce the oxygen content of the RBCs.

As used herein, the terms "red blood cells" and "RBC" include red blood cells or any product which contains red blood cells such as whole blood, packed blood cells and the like, as well as any of those products which have been depleted of white blood cells or platelets and for which prolonged viability of the red cells therein is desired.

In accordance with the invention, the blood storage device is capable of reducing to, or maintaining at, the oxygen content of the RBCs to well below half that obtained in freshly drawn venous blood. In a preferred embodiment, the oxygen content of the RBCs is reduced to or maintained at or below about 15% of full saturation levels and, more preferably, is no greater than about 5–10% and, even more preferably, to below about 1% or less. Alternatively, the blood storage device of the invention is capable of maintaining RBCs wherein reduction in the oxygen content of the RBCs achieves about a 75% survival rate of the RBCs at 24 hours posttransfusion time for cells that have been stored for greater than 6 weeks before the time of transfusion and, more preferably, for cells that have been stored for 10 to 15 weeks or more.

As used herein, "oxygen scrubber material" is a material that irreversibly binds to or combines with oxygen under the conditions of use. For example, the oxygen can chemically react with some component of the material and be converted into another compound. Any material where the off-rate of bound oxygen is zero can serve as an oxygen scavenger. Examples of oxygen scrubber materials oxygen sorbents include iron powders and the like. For example, one oxygen scrubber material commercially available is the product FRESHPAXTM (Multisorb Technologies, Inc., Buffalo, N.Y.)

If oxygen removal is completed prior to introduction of the RBCs to the blood storage device, then it can be accomplished by any method known in the art. For example, a suspension of RBCs can be repeatedly flushed with an inert gas, with or without gentle mixing, until the desired oxygen content is reached or until substantially all of the oxygen has been removed. The inert gas can be argon, helium, nitrogen and the like or any other gas which does not bind to the heme moiety of hemoglobin.

The rate of oxygen removal, whether it occurs in the blood storage device or prior to placing the RBCs into the device, depends on various parameters and can be altered, for example, by selection of oxygen permeable layers which allow oxygen passage at different rates or by selection of the oxygen scrubber. Generally, the oxygen permeability through the layer will be the rate limiting step in the removal of oxygen.

Oxygen removal can be conducted at any temperature that maintains good viability of the RBC. Preferably, oxygen is removed between about 1° C. and about 37° C. provided that RBC viability is maintained.

Once in the blood storage device of the invention, the RBC can be stored under refrigeration in the manner consistent with common industry practice for storage of blood products, preferably at a temperature between 1° C. and 10° C., and more preferably at about 4° C.

Such storage periods range from about 6 to about 20 weeks and longer. Preferred storage periods are about 10 to about 15 weeks duration or longer provided RBC quality is maintained.

As used herein, improved or prolonged shelf life or improved storage of RBCs refers to the preservation of viable RBCs for an extended period of time relative to the current standard of about 6 weeks. In most cases, substantial oxygen removal provides RBCs with an extended storage life of about 10–15 weeks and, in some conditions, up to 20 weeks or greater, particularly when cells are suspended in the storage solutions provided by the subject invention. Storage life can also be prolonged by preventing 2,3-DPG feedback inhibition of the RBC glycolytic pathway.

RBC storage life can be measured by the extent of vesicle the formation, extent of hemolysis, and total cellular ATP levels. Long storage life is obtained when the tesicle formation is low, hemolysis is low and high ATP levels are sustained, preferably above about 2–3 $\mu$mol ATP per g Hb. All of these parameters are measured by the conventional methods known to those of skill in the art. For example, samples of cells can be assayed for the extent of hemolysis by calculating the fraction of supernatant hemoglobin relative to total hemoglobin. To measure ATP levels, for example, RBCs can be assayed for ATP according to the methods described in Technical Bulletins 336-W and 35— (Sigma Chemical Co., St. Louis, Mo.).

The in vitro parameters measured after storage of RBCs provide a means to measure in vivo survival of RBCs. The conventional means to assess in vivo survival is to determine the percentage of cell survival 24 hours post transfusion in a recipient. Typically, the average percentage of cell survival needs to be about or better than 75% to provide an acceptable RBC product. The three parameters, vesicle production, extent of hemolysis, and ATP levels, are routinely used individually in the art to predict in vivo cell survival.

Figure 2:
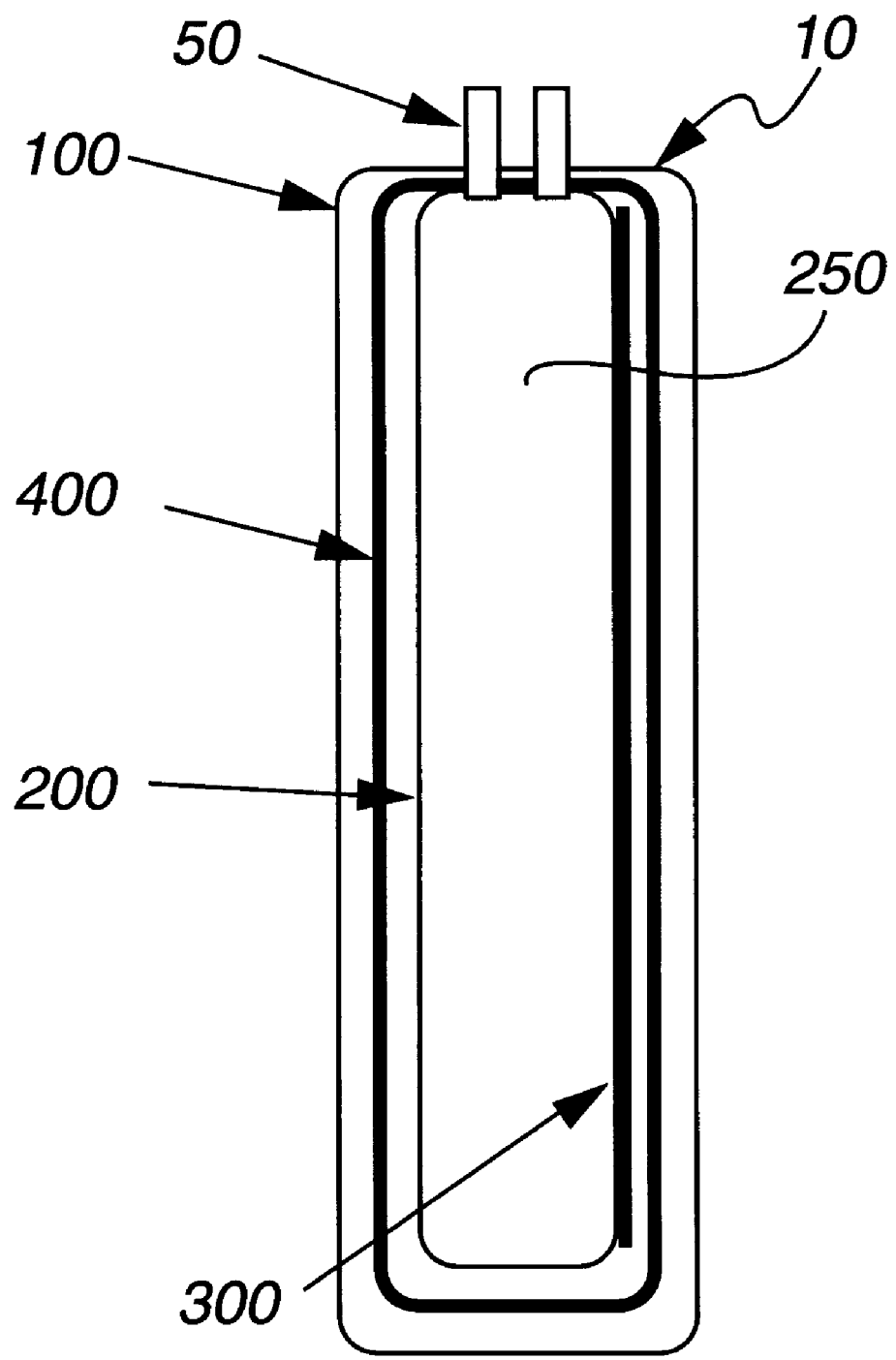
FIG. 2 illustrates a side view of a blood storage device having an oxygen scrubber material between an outer oxygen impermeable layer and an inner oxygen permeable layer wherein the plasticizer is incorporated into the oxygen permeable inner layer.
Figure 3:
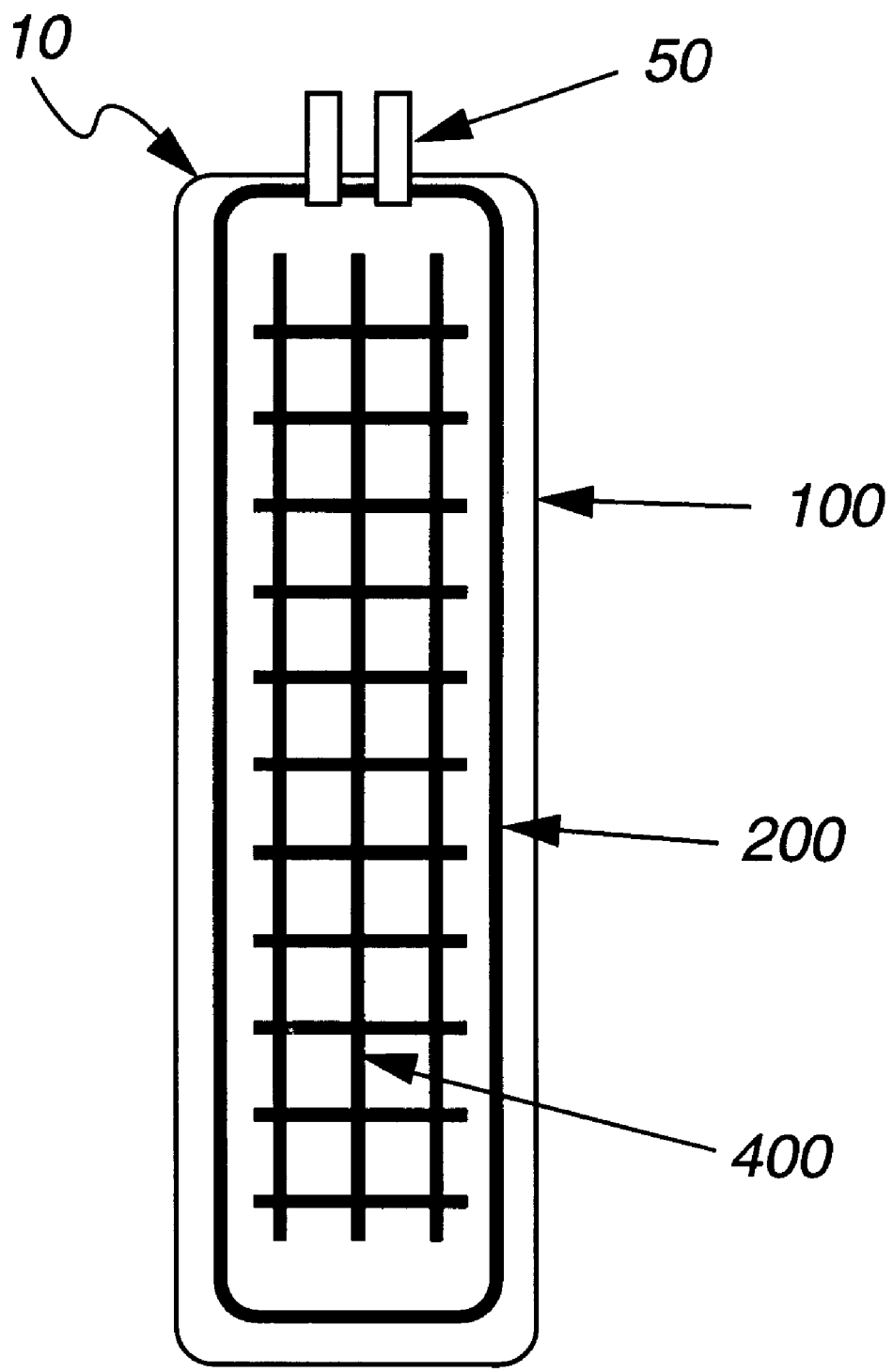
FIG. 3 illustrates a side view of a blood storage device having an oxygen scrubber material encapsulated in CLX plastic within the inner chamber of an inner layer.

FIGS. 1 to 3 show a blood storage device 10 adapted for oxygen removal in accordance with the present invention.

Figure 4:
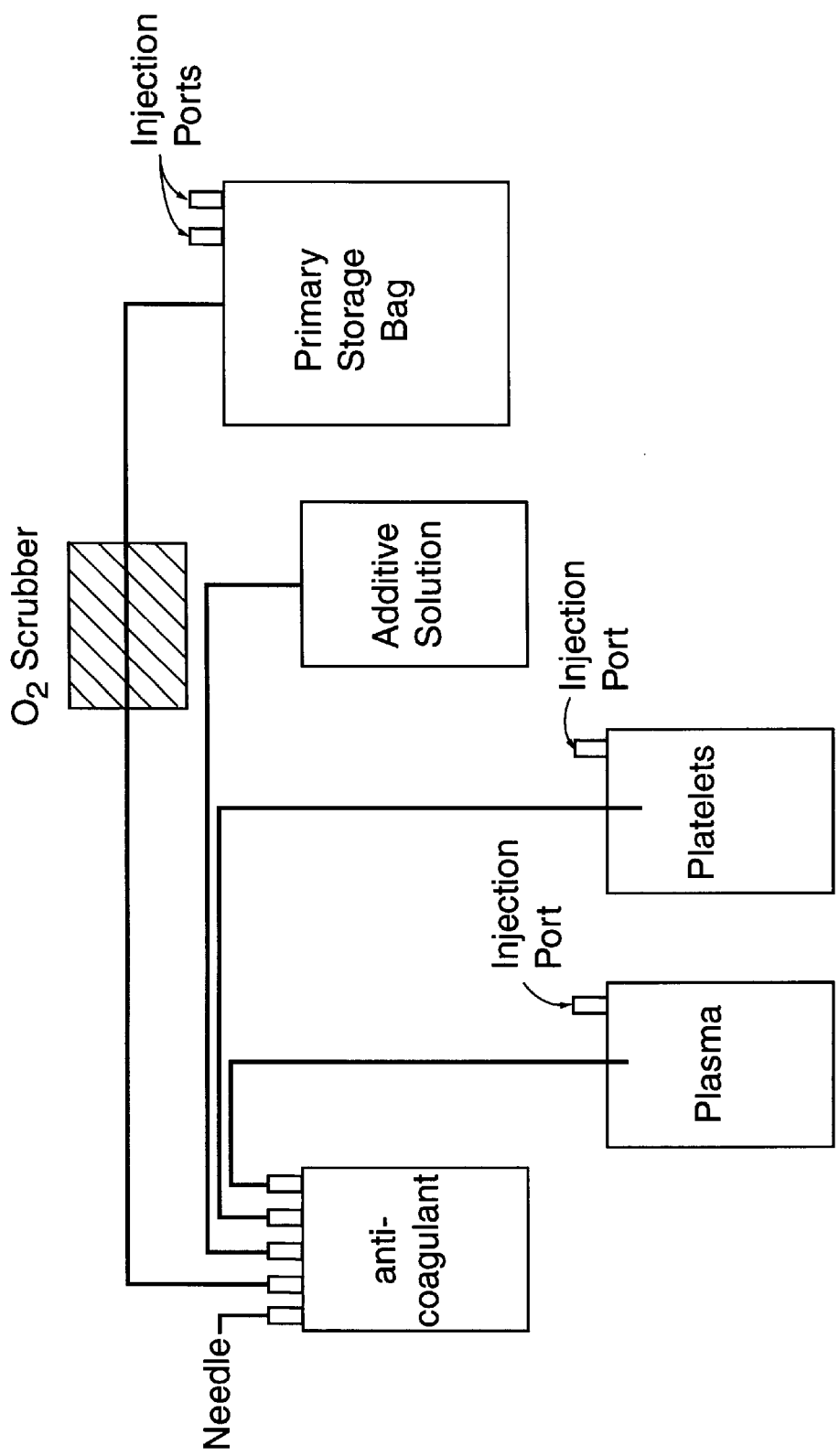
FIG. 4 illustrates a blood collection unit.

The blood storage device of this invention is most conveniently configured as a bag, although any shape container having an oxygen-impermeable outer layer, an oxygen-permeable inner layer, a source of a plasticizer, and a functional oxygen scrubber material is envisaged and can be used. In general the blood storage device of this invention is not the primary collection bag for donated blood. Blood collection units in current use are sterile units which consist of a primary collection bag, and one or more satellite bags connected together in a manner that allows blood or fractions thereof to be moved from one bag to another or that allows a solution in one of the bags to be added to blood or a fraction thereof in another one of the bags (FIG. 4). The blood collection unit is also capable of withstanding the centrifugation used for preparing and collecting the various blood fractions. Hence, the blood storage device of this invention can be added to a blood collection unit as one of the additional satellite bags and is also capable of withstanding the centrifugation forces employed during fractionation of blood and preparation of packed RBCs. The blood storage device is preferably not used as the primary collection bag if the platelets in the blood are to be isolated for use since platelets require oxygen for functioning. In the event, however, that the platelet fraction of the blood is not to be saved, then the blood storage device of this invention can be adapted to serve as a primary blood collection bag and can have satellite bags, as necessary, attached thereto.

To illustrate how a blood collection unit comprising a blood storage device of this invention operates, the following example is given. A blood collection unit includes a primary bag containing an anticoagulant solution and the appropriate connections so that it is attached using sterile techniques to the line of venous blood of the blood donor. This primary bag also can have several satellite bags attached to it in a manner that allows transfer of the blood or the blood component into a satellite bag. After the blood donation is complete, the venous blood intake line is heat-sealed in a sterile manner, and then the entire unit is placed in a centrifuge and spun at a speed to allow collection of the platelets. The platelet-containing supernatant is carefully removed from the top of the bag without mixing the cell layer and transferred to one of the satellite bags, leaving residual plasma and packed RBCs in the primary collection bag. The platelet-containing satellite bag is then removed in a sterile manner, typically by heat sealing the tubing between the primary bag and the satellite bag. The centrifugation can be repeated at a speed to separate more plasma from the RBCs. The plasma is then transferred into a second satellite bag and removed as above. A third satellite bag containing an additive solution for the preservation of the packed RBCs can then be transferred into the primary collection bag, mixed with the RBCs, and finally the RBCs can be transferred to the blood storage device of the invention. Alternatively, the additive solution can be in the blood storage device and the packed RBCs transferred directly thereinto, thus eliminating the need and expense of one satellite bag from the blood collection unit.

Figure 5:
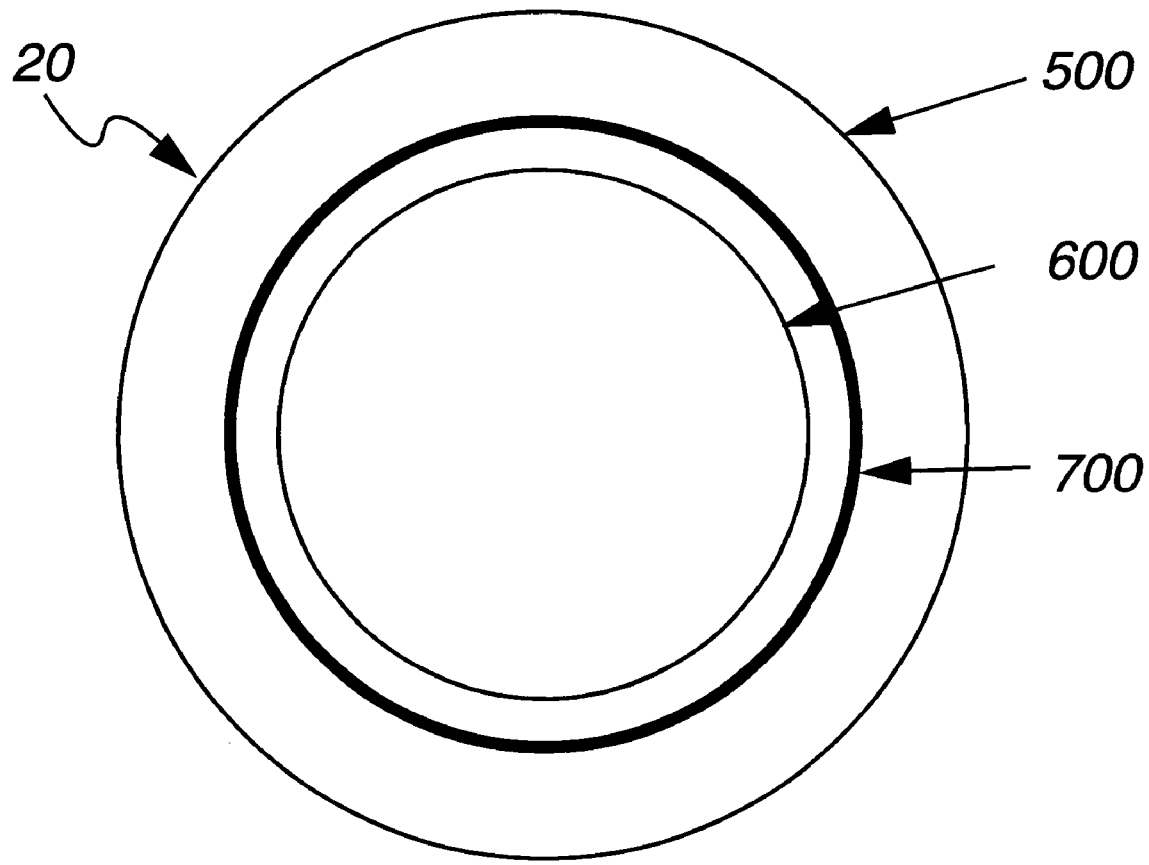
FIG. 5 illustrates a cutaway view of a blood storage device having the outer oxygen impermeable layer, the inner oxygen permeable layer, and the oxygen scrubber material constructed as an in-line initial oxygen removal device.

The blood storage device can also be provided as a separate entity with respect to the blood collection unit so long as there is a means for sterile transfer of the collected blood, RBCS, or other RBC-containing fractions into the blood storage device. Other embodiments of the invention are also possible. For example, the tubing leading from the primary blood collection bag to the blood storage device can be attached to an in-line oxygen removal device as illustrated in FIG. 5. This configuration allows rapid oxygen removal from the RBCs. In another embodiment, the blood storage device can have a satellite bag attached to it provided that such bags are either removable in a manner that leaves an intact oxygen-impermeable outer layer or the satellite bag is composed of an oxygen-impermeable outer layer, again so that the entire blood storage device is oxygen-impermeable.

The overall size of the blood storage device is determined from the desired volume of the inner chamber 250. The inner chamber 250 is designed to hold one unit of blood obtained from an adult donor or the fraction thereof containing the packed RBCs. One unit of blood is about a pint or about 500 ml. Alternatively, the inner chamber can be designed to hold a pediatric unit of blood or a portion thereof. Such a volume can be as low as 75 ml. In another embodiment, the inner chamber volume can be increased so that the packed RBCs can be stored in a diluted form. In such a case, the volume can be about 600–750 ml for diluted RBCs. Once the volume of the inner chamber is chosen, the remainder of the blood storage device can be readily determined by one of ordinary skill in the art.

Referring to FIGS. 1–3, the oxygen impermeable outer Layer 100 is constructed of a material having a high tensile strength to resist breakage. Such material can be an aluminum foil/polymer laminate, a glass fiber/polymer material, or any other suitable laminated materials. Any material which is pliable, yet has a high tensile strength, is oxygen impermeable, does not leach out any harmful substance, is sterilizable, preferably by steam or autoclave, is suitable for the construction of the outer layer 100. As used herein, an oxygen-impermeable material means that permeability of the outer layer 100 to oxygen is less than about 1 nmol/$cm^2$/hr, which is the permeability of the current polyvinyl chloride (PVC) blood collection and storage bags, and preferably is significantly below this level. The outer layer 100 can be opaque or transparent. If the outer layer 100 is opaque, a small observation window constructed of a transparent material having the requisite properties can be incorporated at any convenient position of the outer layer. The transparent material of the window permits visual observation of the stored blood within the blood storage device 10.

Further, the blood storage device 10 has, when appropriate, an oxygen-permeable, RBC-compatible inner layer 200 contained within or fused to the inside of the outer layer 100. The inner layer 200 is contained within the outer layer 100, and the two layers can be separated by the oxygen scrubber material 400.

The inner layer 200 can be a flat surface or, so that it exhibits a large surface area, shaped to be bumpy or as a waffle-like lattice. These latter configurations increase the surface area of the inner layer 200 available to contact the RBCs and can increase the rate of oxygen removal from the RBCs.

The inner layer 200 is constructed of a material that is compatible with red blood cells and thus does not contribute to damage to the red blood cells. Suitable materials for the inner layer are known in the art and described by Carmen (1993) Transfusion Med. Rev. 7:10, The Selection of Plastic Materials for Blood Bags, which is herein expressly incorporated. PVC blood bag materials are currently in use for the storage of blood and, for the most part, do exhibit the requisite oxygen-permeability of the inner layer of this invention. Commercially available blood bag plastics are listed in Table 4 of Carmen. Preferred materials for the inner layer include PL146, PL732 and PL1240 (from Baxter), and CL3861 and CLX3 (from Medsep). All of these are PVC plastic formulations with an added plasticizer except for PL732 which is a polyolefin with no added plasticizer. The oxygen permeability of the material from which the inner layer 200 is constructed ranges from about 10 to about 30 $nmol/cm^2/hr$ and is preferably at least 30 $nmol/cm^2/hr$. In addition to a material's intrinsic oxygen permeability, different levels of oxygen permeability can be achieved by varying the thickness of the material.

Plasticizers of the invention include di(2-ethylhexyl) phthalate (DEPH), tri-(2-ethylhexyl) trimellitate (TEHTM), and any other plasticizers conventionally used to set the PVC polymers and which are compatible with RBCs.

Generally, a plasticizer is added to the inner layer to soften the polymeric material, allow flexibility in the bag, and to enhance RBC storage. In addition, the leaching of the plasticizer is known to prolong RBC storage time by intercalating into the lipid bilayer of the RBCs and stabilizing the cell membrane. If the plasticizer is incorporated into the inner layer, it is generally distributed throughout that material. However, an embodiment of the invention wherein the plasticizer is only on one surface or side of the inner layer is also suitable. Alternatively, if the inner layer contains no plasticizer, then plasticizer can be provided on a ribbon, strip, or lattice as plasticizer delivery device 310. The plasticizer delivery device 310 can be composed of any material suitable for use as the inner layer material and can be in any shape or size, provided it fits easily inside the inner chamber of the blood storage device and does not reduce the volume available for storing the RBCs.

The blood storage device 10 also contains an oxygen scrubber material 400. The oxygen scrubber material 400 is preferably constructed from an iron-based, commercially available material and may be placed variously either between the outer layer 100 and the inner layer 200 or inside the inner chamber 250. As examples for commercial sources, the oxygen scrubber material can be FreshPax™ or other oxygen sorbent products available from Mitsubishi Gas Corp. of Japan. If the oxygen scrubber material is sandwiched between the inner and outer layer of the blood storage device, it can be dispersed evenly throughout that space or it can only be present on one side of the bag if that configuration allows sufficient oxygen absorption/adsorption. The oxygen scrubber material must not penetrate the inner layer of the device to thereby come in contact with the RBCs. If necessary to prevent cross contamination and the like, the oxygen scrubber material found between the inner and outer layer can be encapsulated in an oxygen-permeable material. The physical arrangement of three layers 100, 200 and 400 can be any combination such that all three layers are fused one to another, only two of the layers are fused to each other and the third is in contact with the others but not affixed thereto, or all three layers are in contact with each without being fused together.

The blood storage device 10 has at least two ports 50. One of the ports is an inlet port and serves as the external connection to the blood collection unit when the blood storage device is port of the blood collection unit. Alternatively, the inlet serve as an external connection by which blood or RBCs obtained in another manner can be transferred into the inner chamber 250 of blood storage device 10.

The second port is an injection port and is the port by which the RBCs are removed, e.g., for transfusions and the like. The injection port can also serve as an outlet port. Other ports or additional inlet and injection ports can be added to the blood storage device, if necessary. Preferably, there are two ports, the inlet and the injection port. The ports lead externally from outside the blood storage device 10 to the inner chamber 250 of the device. The ports can be connected by tubing with appropriate connectors attached to heat-sealable tubing that in turn connects with another port of the blood collection unit. The ports are of known material and are conventionally known in the art. Preferably, the ports are constructed of a plastic material, are securely attached to the blood storage device, and are oxygen-impermeable.

Specifically, FIGS. 1 and 2 illustrate the oxygen scrubber material 400 placed between an oxygen impermeable outer layer 100 and an oxygen permeable inner layer 200. The oxygen scrubber material 400 is in close contact with the inner layer 200 and preferably is hermetically sealed at points on the inner layer 200 or fused between the inner and outer layers. Preferably, the scrubber material 400 completely envelopes the inner layer 200, although, depending upon the kinetics of the oxygen absorption of the scrubber material 400 used, complete envelopment may not be necessary and can be limited to, for example, only one side of the blood storage device 10. Furthermore, a plasticizer delivering device 310 is contained within the inner chamber 250 of the inner layer 200 as shown in FIG. 1, or the inner layer 200 contains a plasticizer 300 as shown in FIG. 2.

Referring specifically to FIG. 3, the scrubber material 400 is encapsulated within an oxygen-permeable, RBC-compatible material such as a CLX plastic, polyolefin PL732, or XT162. The encapsulated oxygen scrubber material is contained within inner chamber 250. The shape of the encapsulated oxygen material should provide a large surface area to permit rapid and efficient oxygen removal. Any shape can be used with a fence-like or waffle-like lattice work being preferable. Efficient oxygen removal in the device of FIG. 3 will occur when the oxygen permeability of the encapsulating material is high. In this embodiment, plasticizer is incorporated into the inner layer 200.

Furthermore, referring to FIG. 5, the blood storage device 10 can be constructed with or connected to an in-line, oxygen-removal device 20. This in-line device 20 is attached to the inlet port 50 of the blood storage device 10. The inline device 20 comprises a tube having an oxygen-impermeable outer layer 500, an oxygen-permeable inner layer 600, and an oxygen scrubber material 700 in the arrangement shown in FIG. 5. Preferably, the tube is long and spiral-shaped, and of a sufficient length to permit as much as 90 to 99 percent of the oxygen in the RBCs to be removed during transit of the RBCs down the length of the tube enroute to the blood storage device. After passage through the in-line device, the RBCs are stored in the blood storage device of the invention where any remaining or residual oxygen can be removed.

Alternatively, the in-line device 20 can be constructed to remove a lesser amount of oxygen as the RBCs transit through the tube. In this embodiment, the remainder of oxygen removal can occur in the blood storage device. The oxygen-permeable inner membrane 600 is also red blood cell compatible and is of a thickness which maximizes the oxygen permeability. The materials used to construct inner layer 600, the scrubber material 700, and the oxygen impermeable outer layer 500 are the same as those used in the corresponding components of the blood storage device 10. In addition, the inner layer 600 can be medical grade GoreTex™.

It is to be understood and expected that variations in the principles of construction herein disclosed in an exemplary embodiment may be made by one skilled in the art and it is intended that such modifications, changes, and substitutions are to be included within the scope of the present invention.

What is claimed is:

1. A blood storage device for removal of oxygen from blood, comprising:
    an oxygen-impermeable outer layer;
    a red blood cell compatible inner layer; and
    an oxygen scrubber material placed internal to said inner layer, and encapsulated in an oxygen-permeable, red blood cell compatible material, wherein said outer layer and inner layers form a chamber adapted to contain red blood cells or blood.

2. The device of claim 1, wherein said inner layer contains a plasticizer.

3. The device of claim 1, wherein the chamber contains a plasticizer-delivery device.

4. The device of claim 1, further comprising: at least two ports, wherein at least one of said ports allows transfer of blood or red blood cells into the chamber and at least one of said ports allows transfer of blood or red blood cells out of the chamber.

5. The device of claim 1, wherein the oxygen scrubber material is encapsulated in a lattice having a large surface area such that rapid and efficient oxygen removal occurs.

6. The device of claim 4, wherein an in-line oxygen removal device is connected in series with said at least one port which allows transfer of blood into the chamber of the blood storage device.

* * * * *